(12) United States Patent
Akeboshi et al.

(10) Patent No.: US 8,476,470 B2
(45) Date of Patent: Jul. 2, 2013

(54) PROCESS FOR PRODUCTION OF BICYCLO[2.2.2]OCTYLAMINE DERIVATIVE

(75) Inventors: Tomohiro Akeboshi, Chiba (JP); Yusuke Iriyama, Chiba (JP); Hirotaka Kawanami, Yamaguchi (JP)

(73) Assignee: Kyorin Pharmaceutical Co., Ltd., Tokyo (JP)

( * ) Notice: Subject to any disclaimer, the term of this patent is extended or adjusted under 35 U.S.C. 154(b) by 248 days.

(21) Appl. No.: 13/057,879

(22) PCT Filed: Aug. 7, 2009

(86) PCT No.: PCT/JP2009/064049
§ 371 (c)(1),
(2), (4) Date: Feb. 7, 2011

(87) PCT Pub. No.: WO2010/016584
PCT Pub. Date: Feb. 11, 2010

(65) Prior Publication Data
US 2011/0137070 A1 Jun. 9, 2011

(30) Foreign Application Priority Data
Aug. 7, 2008 (JP) ................................. 2008-204447

(51) Int. Cl.
*C07C 62/20* (2006.01)
(52) U.S. Cl.
USPC .......................................... 560/120; 560/118
(58) Field of Classification Search
USPC ................................................ 560/120, 118
See application file for complete search history.

(56) References Cited

U.S. PATENT DOCUMENTS

| | | | |
|---|---|---|---|
| 3,301,827 A | 1/1967 | Martin | |
| 3,347,919 A | 10/1967 | Martin | |
| 5,939,560 A | 8/1999 | Jenkins et al. | |
| 5,965,764 A | 10/1999 | Matsuoka et al. | |
| 6,020,370 A * | 2/2000 | Horwell et al. | 514/511 |
| 6,166,063 A | 12/2000 | Villhauer | |
| 6,303,661 B1 | 10/2001 | Demuth et al. | |
| 6,432,969 B1 | 8/2002 | Villhauer | |
| 6,849,622 B2 | 2/2005 | Yasuda et al. | |
| 7,132,443 B2 | 11/2006 | Haffner et al. | |
| 7,138,397 B2 | 11/2006 | Yasuda et al. | |
| 7,160,877 B2 | 1/2007 | Yasuda et al. | |
| 7,183,290 B2 | 2/2007 | Haffner et al. | |
| 7,196,201 B2 | 3/2007 | Haffner et al. | |
| 7,268,150 B2 | 9/2007 | Hayakawa et al. | |
| 7,332,487 B2 | 2/2008 | Yasuda et al. | |
| 7,348,327 B2 | 3/2008 | Aranyi et al. | |
| 7,514,571 B2 | 4/2009 | Fukuda et al. | |
| 7,560,569 B2 * | 7/2009 | Fukuda et al. | 548/200 |
| 7,666,869 B2 | 2/2010 | Yasuda et al. | |
| 7,754,757 B2 | 7/2010 | Fukuda et al. | |
| 2001/0025023 A1 | 9/2001 | Carr | |
| 2001/0031780 A1 | 10/2001 | Kanstrup et al. | |
| 2002/0006899 A1 | 1/2002 | Pospisilik et al. | |
| 2002/0019339 A1 | 2/2002 | Naughton | |
| 2002/0019411 A1 | 2/2002 | Robl et al. | |
| 2002/0037829 A1 | 3/2002 | Aronson et al. | |
| 2002/0103384 A1 | 8/2002 | Kanstrup et al. | |
| 2002/0110560 A1 | 8/2002 | Demuth et al. | |
| 2002/0193390 A1 | 12/2002 | Villhauer | |
| 2003/0100563 A1 | 5/2003 | Edmondson et al. | |

(Continued)

FOREIGN PATENT DOCUMENTS

| | | |
|---|---|---|
| EP | 1 712 547 | 10/2006 |
| JP | 09-509921 | 10/1997 |

(Continued)

OTHER PUBLICATIONS

Simon et al; Synlett, 2003, 15, 2301-2304.*

(Continued)

*Primary Examiner* — Johann R Richter
*Assistant Examiner* — Pancham Bakshi
(74) *Attorney, Agent, or Firm* — Wenderoth, Lind & Ponack, L.L.P.

(57) ABSTRACT

The present invention herein provides a process for production of a bicyclo[2.2.2]octylamine derivative which may be used as an intermediate for preparation of medical and pharmaceutical products. The process is quite efficient and can produce the derivative in a large-scale while using mild reaction conditions.

The process for producing a bicyclo[2.2.2]octylamine derivative comprises the steps of subjecting, to ring-formation, a compound represented by the following general formula (1):

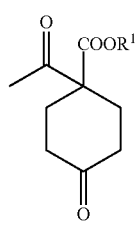

(1)

[wherein $R^1$ represents an alkyl group having 1 to 6 carbon atoms, which may have a substituent; an arylmethyl group which may have a substituent; or an arylethyl group which may have a substituent], and a compound represented by the following general formula (2):

$R^2$—$NH_2$  (2)

[wherein $R^2$ represents an alkyl group having 1 to 6 carbon atoms, which may have a substituent; an aralkyl group which may have a substituent; a hydroxyl group; an alkyloxy group having 1 to 6 carbon atoms, which may have a substituent; or an aralkyloxy group which may have a substituent], and then reducing the resulting product.

10 Claims, No Drawings

U.S. PATENT DOCUMENTS

| | | |
|---|---|---|
| 2003/0105077 A1 | 6/2003 | Kanstrup et al. |
| 2003/0176357 A1 | 9/2003 | Pospisilik et al. |
| 2003/0225102 A1 | 12/2003 | Sankaranarayanan |
| 2004/0017848 A1 | 1/2004 | Doan et al. |
| 2004/0063935 A1 | 4/2004 | Yasuda et al. |
| 2004/0072892 A1 | 4/2004 | Fukushima et al. |
| 2004/0082607 A1 | 4/2004 | Oi et al. |
| 2004/0106655 A1 | 6/2004 | Kitajima et al. |
| 2004/0106802 A1 | 6/2004 | Sankaranarayanan |
| 2004/0121964 A1 | 6/2004 | Madar et al. |
| 2004/0152745 A1 | 8/2004 | Jackson et al. |
| 2004/0167133 A1 | 8/2004 | Edmondson et al. |
| 2004/0167341 A1 | 8/2004 | Haffner et al. |
| 2004/0176428 A1 | 9/2004 | Edmondson et al. |
| 2004/0229926 A1 | 11/2004 | Yasuda et al. |
| 2004/0242636 A1 | 12/2004 | Haffner et al. |
| 2005/0054678 A1 | 3/2005 | Yasuda et al. |
| 2005/0070719 A1 | 3/2005 | Belyakov et al. |
| 2005/0107308 A1 | 5/2005 | Pospisilik et al. |
| 2005/0107309 A1 | 5/2005 | Demuth et al. |
| 2005/0130981 A1 | 6/2005 | Aranyl et al. |
| 2005/0148606 A1 | 7/2005 | Kanstrup et al. |
| 2005/0153973 A1 | 7/2005 | Aranyl et al. |
| 2005/0164989 A1 | 7/2005 | Abe et al. |
| 2005/0176771 A1 | 8/2005 | Hayakawa et al. |
| 2005/0245538 A1 | 11/2005 | Kitajima et al. |
| 2005/0266080 A1 | 12/2005 | Desai et al. |
| 2006/0142585 A1 | 6/2006 | Thomas et al. |
| 2006/0173056 A1 | 8/2006 | Kitajima et al. |
| 2006/0210627 A1 | 9/2006 | Pfeffer et al. |
| 2006/0241146 A1 | 10/2006 | Yasuda et al. |
| 2006/0270679 A1 | 11/2006 | Edmondson et al. |
| 2007/0112059 A1 | 5/2007 | Fukushima et al. |
| 2007/0112205 A1 | 5/2007 | Fukushima et al. |
| 2007/0167501 A1 | 7/2007 | Fukuda et al. |
| 2007/0265320 A1 | 11/2007 | Fukuda et al. |
| 2008/0038341 A1 | 2/2008 | Kowalski et al. |
| 2008/0050443 A1 | 2/2008 | Kowalski et al. |
| 2008/0146818 A1 | 6/2008 | Fukuda et al. |
| 2008/0176870 A1 | 7/2008 | Nolte et al. |
| 2009/0048454 A1 | 2/2009 | Asahina et al. |
| 2010/0093825 A1 | 4/2010 | Fukuda et al. |
| 2010/0099892 A1 | 4/2010 | Orita et al. |
| 2011/0137070 A1 | 6/2011 | Akeboshi et al. |
| 2011/0152342 A1 | 6/2011 | Uchida et al. |
| 2011/0172444 A1 | 7/2011 | Shiga |

FOREIGN PATENT DOCUMENTS

| | | |
|---|---|---|
| JP | 11-512096 | 10/1999 |
| JP | 11-322701 | 11/1999 |
| JP | 2000-511559 | 9/2000 |
| JP | 2001-261644 | 9/2001 |
| JP | 2002-531547 | 9/2002 |
| JP | 2002-356471 | 12/2002 |
| JP | 2002-356472 | 12/2002 |
| JP | 2003-520849 | 7/2003 |
| JP | 2003-531118 | 10/2003 |
| JP | 2003-535034 | 11/2003 |
| JP | 2004-2367 | 1/2004 |
| JP | 2004-2368 | 1/2004 |
| JP | 2004-26820 | 1/2004 |
| JP | 2004-503531 | 2/2004 |
| JP | 2005-500321 | 1/2005 |
| JP | 2005-529078 | 9/2005 |
| JP | 2005-532369 | 10/2005 |
| JP | 2006-160733 | 6/2006 |
| JP | 2007-518760 | 7/2007 |
| JP | 2008-501025 | 1/2008 |
| JP | 2008-510764 | 4/2008 |
| JP | 2008-527004 | 7/2008 |
| JP | 2008-530229 | 8/2008 |
| JP | 2008-534436 | 8/2008 |
| JP | 2008-239543 | 10/2008 |
| JP | 2008-290969 | 12/2008 |
| JP | 2008-543773 | 12/2008 |
| JP | 2009-114127 | 5/2009 |
| JP | 2010-70454 | 4/2010 |
| WO | 95/15309 | 6/1995 |
| WO | 97/40832 | 11/1997 |
| WO | 98/19998 | 5/1998 |
| WO | 00/34241 | 6/2000 |
| WO | 01/34594 | 5/2001 |
| WO | 01/55105 | 8/2001 |
| WO | 01/62266 | 8/2001 |
| WO | 01/68603 | 9/2001 |
| WO | 01/96295 | 12/2001 |
| WO | 02/14271 | 2/2002 |
| WO | 02/30890 | 4/2002 |
| WO | 02/30891 | 4/2002 |
| WO | 02/38541 | 5/2002 |
| WO | 02/062764 | 8/2002 |
| WO | 03/000180 | 1/2003 |
| WO | 03/002530 | 1/2003 |
| WO | 03/002531 | 1/2003 |
| WO | 03/002553 | 1/2003 |
| WO | 03/004496 | 1/2003 |
| WO | 03/004498 | 1/2003 |
| WO | 03/015775 | 2/2003 |
| WO | 03/017936 | 3/2003 |
| WO | 03/057144 | 7/2003 |
| WO | 03/057666 | 7/2003 |
| WO | 03/074500 | 9/2003 |
| WO | 03/080633 | 10/2003 |
| WO | 03/084940 | 10/2003 |
| WO | 03/095425 | 11/2003 |
| WO | 03/106456 | 12/2003 |
| WO | 2004/007446 | 1/2004 |
| WO | 2004/009544 | 1/2004 |
| WO | 2004/026822 | 4/2004 |
| WO | 2004/099185 | 11/2004 |
| WO | 2005/067976 | 7/2005 |
| WO | 2005/075421 | 8/2005 |
| WO | 2005/077900 | 8/2005 |
| WO | 2005/082847 | 9/2005 |
| WO | 2005/117841 | 12/2005 |
| WO | 2006/021455 | 3/2006 |
| WO | 2006/040625 | 4/2006 |
| WO | 2006/043595 | 4/2006 |
| WO | 2006/078593 | 7/2006 |
| WO | 2006/135723 | 12/2006 |
| WO | 2007/102286 | 9/2007 |
| WO | 2007/142253 | 12/2007 |
| WO | 2008/063671 | 5/2008 |
| WO | 2008/096841 | 8/2008 |
| WO | 2010/016584 | 2/2010 |
| WO | 2010/018866 | 2/2010 |
| WO | 2010/032723 | 3/2010 |

OTHER PUBLICATIONS

S. Efendid, et al., International Journal of Gastroenterology, "Glucagon-Like Insulinotropic Peptide Has a Stronger Antidiabetogenic Effect than Glibenclamide", Digestion, vol. 54, 1993, pp. 392-393.*

International Search Report issued Sep. 8, 2009 in International (PCT) Application No. PCT/JP2009/064049.

PCT Written Opinion of the International Searching Authority Sep. 8, 2009 in International (PCT) Application No. PCT/JP2009/064049.

Della et al., "Synthesis of Bridgehead-Bridgehead Substituted Bicycloalkanes", Aust. J. Chem., vol. 38, pp. 1705-1718 (1985).

Grob et al., "Die Synthese von 4-substituierten Bicyclo[2.2.2]oct-l-yl-$p$-nitrobenzosulfonaten" Helvetica Chimica Acta, vol. 62, No. 8, pp. 2802-2816 (1979).

Ahmed et al., "Enamine Chemistry. Part 26. Preparation of Substituted Adamantane-2,4-diones and Bicyclo[2.2.2]octan-2-ones", J. Chem. Soc. Perkin 1, pp. 2180-2183 (1979).

Morita et al., "A Novel Cyclization of 4-Acetyl-1-methoxy-1-cyclohexene to 4-Alkoxybicyclo[2.2.2]octan-2-ones" J. Org. Chem., vol. 31, pp. 229-232 (1966).

Seebacher et al., "Structural Requirements for the Antiprotozoal Activity of 4-Aminobicyclo[2.2.2]octan-2-ols", Monatshefte fur Chemie, vol. 137, pp. 471-482 (2006).

Roberts et al., "Syntheses of Some 4-Substituted Bicyclo[2.2.2]octane-1-carboxylic Acids" J. Am. Chem. Soc., vol. 75, pp. 637-640 (1953).

International Search Report issued May 1, 2007 in the International (PCT) Application PCT/JP2007/051768.
Edwin B. Villhauer et al., "1-[[(3-Hydroxy-1-adamantyl)amino]acetyl]-2-cyano-(S)-pyrrolidine: A Potent,Selective, and Orally Bioavailable Dipeptidyl Peptidase IV Inhibitor with Antihyperglycemic Properties",J. Med. Chem., 46, pp. 2774-2789, 2003.
Hiroshi Fukushima et al., "Synthesis and structure-activity relationships of potent 3- or 4-substituted-2-cyanopyrrolidine dipeptidyl peptidase IV inhibitors", Bioorganic & Medicinal Chemistry, 12, pp. 6053-6061, 2004.
International Search Report issued May 13, 2008 with Written Opinion in International (PCT) Application No. PCT/JP2008/055202 (with English translation).
International Search Report issued Mar. 15, 2005 with Written Opinion in International (PCT) Application No. PCT/JP2005/001377 (with English translation).
Japanese Office Action issued Jan. 9, 2007 in Japanese Application No. 2005-517671 (with English translation).
U.S. Office Action issued Apr. 3, 2009 in U.S. Appl. No. 10/588,660.
U.S. Office Action issued Oct. 20, 2008 in U.S. Appl. No. 10/588,660.
New Zealand Office Action issued Feb. 12, 2009 in New Zealand Patent Application No. 548440.
Australian Office Action issued Oct. 9, 2007 in Australian Application No. 2005210285.
Chinese Office Action issued Oct. 17, 2008 in Chinese Application No. 200580004191.8 (English Translation only).
Chinese Office Action issued Jun. 5, 2009 in Chinese Application No. 200580004191.8 (English translation only).
Supplementary European Search Report issued Aug. 23, 2007 in European Application No. 05 70 4327.
International Search Report issued Mar. 29, 2005, International Preliminary Report on Patentability issued Sep. 19, 2006 with Written Opinion in International (PCT) Application No. PCT/JP2005/002389 (with English translation).
U.S. Office Action issued Oct. 15, 2008 in U.S. Appl. No. 10/590,111.
Chinese Office Action issued Aug. 8, 2008 in Chinese Application No. 200580005175.0 (English translation only).
International Search Report issued May 10, 2005, International Preliminary Report on Patentability issued Sep. 19, 2006 with Written Opinion in International (PCT) Application No. PCT/JP2005/002806 (with English translation).
U.S. Office Action issued Dec. 21, 2007 in U.S. Appl. No. 10/590,871.
U.S. Office Action issued Aug. 22, 2008 in U.S. Appl. No. 10/590,871.
International Search Report issued Mar. 4, 2008 with Written Opinion in International (PCT) Application No. PCT/JP2008/052096 (with English translation).
C. F. Deacon, et al., "Glucagon-like peptide 1 undergoes differential tissue-specific metabolism in the anesthetized pig", American Journal of Physiology, 1996, vol. 271, pp. E458-E464.
L.B. Knudsen, et al., "Glucagon-like peptide-1-(9-36) amide is a major metabolite of glucagon-like peptide-1-(7-36) amide after in vivo administration to dogs, and it acts as an antagonist on the pancreatic receptor", European Journal of Pharmacology, 1996, vol. 318, pp. 429-435.
E.G. Siegel, et al., "Comparison of the effect of GIP and GLP-1 (7-36amide) on insulin release from rat pancreatic islets", European Journal of Clinical Investigation, 1992, vol. 22, pp. 154-157.
B. Kreymann, et al., "Glucagon-Like Peptide-1 7-36: A Physiological Incretin in Man", The Lancet, 1987, vol. 2, pp. 1300-1303.
H. Fehmann, et al., "Insulinotropic Hormone Glucagon-like Peptide-I(7-37) Stimulation of Proinsulin Gene Expression and Proinsulin Biosynthesis in Insulinoma βTC-1 Cells", Endocrinology, 1992, vol. 130, No. 1, pp. 159-166.
J. Buteau, et al., "Glucagon-like peptide-1 promotes DNA synthesis, activates phosphatidylinositol 3-kinase and increases transcription factor pancreatic and duodenal homeobox gene 1 (PDX-1) DNA binding activity in beta (INS-1)-cells", Diabetologia, 1999, vol. 42, pp. 856-864.

J. M. Egan, et al., "Glucagon-Like Peptide-1(7-36) Amide (GLP-1) Enhances Insulin-Stimulated Glucose Metabolism in 3T3-L1 Adipocytes: One of Several Potential Extrapancreatic Sites of GLP-1 Action", Endocrinology, 1994, vol. 135 No. 1, pp. 2070-2075.
M.L. Villanueva-Peñacarrillo, et al., "Potent glycogenic effect of GLP-1(7-36)amide in rat skeletal muscle", Diabetologia, 1994, vol. 37, pp. 1163-1166.
M. Anvari, et al., "Effects of GLP-1 on Gastric Emptying, Antropyloric Motility, and Transpyloric Flow in Response to a Nonnutrient Liquid", Digestive Diseases and Sciences, 1998, vol. 43, No. 6, pp. 1133-1140.
J. Holst, et al., "Inhibition of the Activity of Dipeptidyl-Peptidase IV as a Treatment for Type 2 Diabetes", Diabetes, 1998, vol. 47, pp. 1663-1670.
B. Balkan, et al , "Inhibition of dipeptidyl peptidase IV with NVP-DPP728 increases plasma GLP-1 (7-36 amide) concentrations and improves oral glucose tolerance in obese Zucker rats," Diabetologia, 1999, vol. 42, pp. 1324-1331.
M. V. Blazquez, et al., "Selective Decrease of CD26 Expression in T Cells From HIV-1-Infected Individuals", The Journal of Immunology, 1992, vol. 149, No. 9, pp. 3073-3077.
M. Subramanyam, et al., "Mechanism of HIV-1 Tat Induced Inhibition of Antigen-Specific T Cell Responsiveness", The Journal of Immunology, 1993, vol. 150, No. 6, pp. 2544-2553.
E. Schön, et al., "Dipeptidyl Peptidase IV in the Immune System—Effects of Specific Enzyme Inhibitors on Activity of Dipeptidyl Peptidase IV and Proliferation of Human Lymphocytes", Biological Chemistry Hoppe-Seyler, 1991, vol. 372, pp. 305-311.
T. Mattern, et al., "Expression of CD26 (Dipeptidyl Peptidase IV) on Resting and Activated Human T-Lymphocytes", Scandinavian Journal of Immunology, 1991, vol. 33, pp. 737-748.
E. Schön, et al., "Dipeptidyl Peptidase IV in Human T Lymphocytes—Impaired Induction of Interleukin 2 and Gamma Interferon Due to Specific Inhibition of Dipeptidyl Peptidase IV", Scandinavian Journal of Immunology, 1989, vol. 29, pp. 127-132.
J. Kameoka, et al., "Direct Association of Adenosine Deaminase with a T Cell Activation Antigen, CD26", Science, 1993, vol. 261, pp. 466-469.
F. Raynaud, et al., "Characterization of Specific Proteases Associated With the Surface of Human Skin Fibroblasts, and Their Modulation in Pathology", Journal of Cellular Physiology, 1992, vol. 151, pp. 378-385.
G. Vanhoof, et al., "Distribution of Proline-Specific Aminopeptidases in Human Tissues and Body Fluids", European Journal of Clinical Chemistry and Clinical Biochemistry, 1992, vol. 30, No. 6, pp. 333-338.
R. C. Johnson, et al., "Lung Endothelial Dipeptidyl Peptidase IV is an Adhesion Molecule for Lung-metastatic Rat Breast and Prostate Carcinoma Cells", The Journal of Cell Biology, 1993, vol. 121, No. 6, pp. 1423-1432.
E. W. Della, et al., "Synthesis of Bridgehead-Bridgehead Substituted Bicycloalkanes", Australian Journal of Chemistry, 1985, vol. 38, pp. 1705-1718.
C. A. Grob, et al., "283. Die Synthese von 4-substituierten Bicyclo[2.2.2]oct-1-yl-$p$-nitrobenzolsulfonaten", Helvetica Chimica Acta, 1979, vol. 62, pp. 2802-2817.
S. A. Ahmed, et al., "Enamine Chemistry. Part 26. Preparation of Substituted Adamantane-2,4-diones and Bicyclo[2.2.2]octan-2-ones", Journal of Chem. Soc., Perkin I, 1979, pp. 2180-2183.
K. Morita, et al., "A Novel Cyclization of 4-Acetyl-1-methoxy-1-cyclohexene to 4-Alkoxybicyclo[2.2.2]octan-2-ones", J. Org. Chem., 1966, vol. 31, pp. 229-232.
J. D. Roberts, et al., "Syntheses of Some 4-Substituted Bicyclo [2.2.2]octane-1-carboxcylic Acids", J. Am. Chem. Soc., 1953, vol. 75, pp. 637-640.
International Preliminary Report on Patentability dated Sep. 9, 2008 with translation of PCT Written Opinion for PCT/JP2007/051768.
Supplementary European Search Report issued Nov. 23, 2011 in European Application No. 09 80 5066.
W. Seebacher, et al., "Structural Requirements for the Antiprotozoal Activity of 4-Aminobicyclo[2.2.2]octan-2-ols", Monatshefte für Chemie, 2006, vol. 137, pp. 471-482.

* cited by examiner

PROCESS FOR PRODUCTION OF BICYCLO[2.2.2]OCTYLAMINE DERIVATIVE

INDUSTRIAL FIELD OF THE INVENTION

The present invention relates to a process for production of a bicyclo[2.2.2]octylamine derivative.

BACKGROUND ART

A bicyclo[2.2.2]octylamine derivative represented by the following general formula (8) is important as a raw material for preparing pharmaceutical products such as drugs for treating diabetes (Patent Documents 1 to 3):

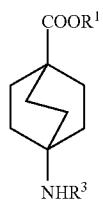

(8)

[in the formula (8), $R^1$ represents an alkyl group having 1 to 6 carbon atoms, which may have a substituent; an arylmethyl group which may have a substituent; or an arylethyl group which may have a substituent; and $R^3$ represents a hydrogen atom, an alkyl group having 1 to 6 carbon atoms, which may have a substituent, or an aralkyl group which may have a substituent.

In Patent Documents 1 to 3, the bicyclo[2.2.2]octylamine derivative is prepared from, for instance, a bicyclo[2.2.2]octyldicarboxylic acid derivative. However, these Patent Documents 1 to 3 do not disclose, at all, the process for preparing a bicyclo[2.2.2]octylamine derivative by forming the bicyclo[2.2.2]octane skeleton while simultaneously linking an amine compound to the skeleton.

Non-Patent Documents 1 to 6 disclose processes for preparation of bicyclo compounds.

However, Non-Patent Document 1 relates to a process for preparation of a bicyclo[2.2.2]octyldicarboxylic acid derivative by reacting cyclohexyl-1,4-dicarboxylate with 1-bromo-2-chloroethane and does not relate to a process for preparing a bicyclo[2.2.2]octylamine derivative using an amine compound. For this reason, the process of Non-Patent Document 1 requires the use of a reaction to be carried out at low temperature and accordingly, this process should use quite expensive reagents.

Non-Patent Documents 2 and 6 also disclose processes for reducing the carbonyl group of a bicyclo[2.2.2]octane skeleton after the formation of the latter. In these articles, the carbonyl group is reduced after it is converted into a dithiane derivative or a dithiolane derivative.

The techniques disclosed in Non-Patent Documents 3 and 5 relate to processes for preparing bicyclo[2.2.2]octylamine derivatives, in which a secondary amine compound is linked to a bicyclo[2.2.2]octane skeleton simultaneous with the formation of the latter. However, these prior articles never disclose the process for preparation of a bicyclo[2.2.2]octylamine derivative by the linkage of a primary amine compound to such a bicyclo[2.2.2]octane skeleton.

Even in Non-Patent Document 4, there is disclosed a process for formation of a bicyclo[2.2.2]octyl skeleton, but this article does not disclose the process for preparing a bicyclo[2.2.2]octylamine derivative by forming the bicyclo-[2.2.2]octane skeleton while simultaneously linking an amine compound to the skeleton.

PRIOR ART LITERATURE

Patent Document

Patent Document 1: WO 2005/075421 Pamphlet;
Patent Document 2: WO 2005/077900 Pamphlet;
Patent Document 3: WO 2005/082847 Pamphlet.

Non-Patent Document

Non-Patent Document 1: Australian J. Chem., 1985, 38(11): 1705-1718;
Non-Patent Document 2: Helv. Chim. Acta., 1979, 62: 2802-2816;
Non-Patent Document 3: J. Chem. Soc. Prekin I, 1979, 2180-2183;
Non-Patent Document 4: J. Org. Chem., 1966, 31: 229-232;
Non-Patent Document 5: Montshefte fuer Chemie, 2006, 137: 471-482;
Non-Patent Document 6: J. Am. Chem. Soc., 1953, 75: 637-641.

SUMMARY OF THE INVENTION

Subject to be Attained by the Invention

Hitherto, there has been known the process for production of bicyclo [2.2.2]octylamine derivative, but the process for production of a bicyclo[2.2.2]octylamine derivative represented by the general formula (8) is not suitable for the large-scale production of the same, does not provide any product in high yield and has a relatively high content of decomposed products as contaminants.

Accordingly, it is the subject of the present invention to provide a process for production of a bicyclo[2.2.2]octylamine derivative represented by the general formula (8), which is quite efficient and permits the large-scale synthesis of the derivative while making use of mild conditions.

Means for Attaining the Subject

The inventors of this present invention have intensively conducted studies to develop a process for production of a bicyclo[2.2.2]octylamine derivative represented by the general formula (8), which is quite efficient and permits the large-scale synthesis of the derivative, and as a result, have found that a process, which can ensure the achievement of a high production efficiency and which does not use any low temperature reaction, would permit the efficient production of the same under mild conditions and have thus completed the present invention.

More specifically, the present invention relates to inventions detailed below.

[1] A process for production of a compound represented by the following general formula (4) comprising the following steps:

(Step 1): a step for reacting a compound represented by the following general formula (1):

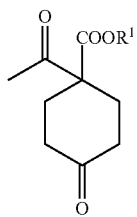

(1)

[in the formula (1), $R^1$ represents an alkyl group having 1 to 6 carbon atoms, which may have a substituent; an arylmethyl group which may have a substituent; or an arylethyl group which may have a substituent], with a compound represented by the following general formula (2):

$R^2$—$NH_2$ (2)

[in the formula (2), $R^2$ represents an alkyl group having 1 to 6 carbon atoms, which may have a substituent; an aralkyl group which may have a substituent; a hydroxyl group; an alkyloxy group having 1 to 6 carbon atoms, which may have a substituent; or an aralkyloxy group which may have a substituent], to thus form a compound represented by the following general formula (3):

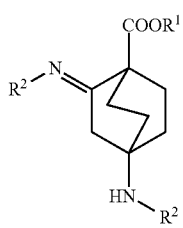

(3)

[in the formula (3), $R^1$ and $R^2$ are the same as those defined above]; and (Step 2): a step for hydrolyzing the compound represented by the general formula (3) to form a compound represented by the following general formula (4):

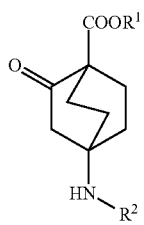

(4)

[in the formula (4), $R^1$ and $R^2$ are the same as those defined above].

[2] The process as set forth in the foregoing item [1], wherein the amount of the compound represented by the general formula (2) is not less than 2 equivalents relative to that of the compound represented by the general formula (1).

[3] The process as set forth in the foregoing item [1] or [2], wherein the compound represented by the general formula (3) is hydrolyzed in the presence of an acid.

[4] A process for production of a compound represented by the following general formula (8) comprising the following steps:

(Step 3): a step for reducing a compound represented by the following general formula (4):

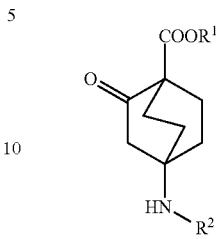

(4)

[in the formula (4), $R^1$ represents an alkyl group having 1 to 6 carbon atoms, which may have a substituent; an arylmethyl group which may have a substituent; or an arylethyl group which may have a substituent; and $R^2$ represents an alkyl group having 1 to 6 carbon atoms, which may have a substituent; an aralkyl group which may have a substituent; a hydroxyl group; an alkyloxy group having 1 to 6 carbon atoms, which may have a substituent; or an aralkyloxy group which may have a substituent], to thus form a compound represented by the following general formula (5):

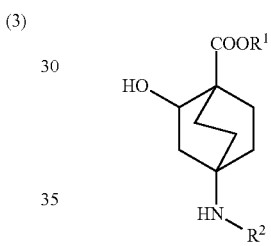

(5)

[in the formula (5), $R^1$ and $R^2$ are the same as those defined above];

(Step 4): a step for reacting the compound represented by the general formula (5) with a halogenating agent, an alkylsulfonating agent having 1 to 6 carbon atoms, which may have a substituent, or a benzenesulfonating agent which may have a substituent to thus form a compound represented by the following general formula (6):

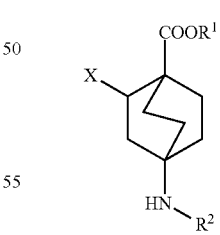

(6)

[in the formula (6), X represents a halogen atom, an alkylsulfonyloxy group having 1 to 6 carbon atoms, which may have a substituent, or a benzenesulfonyloxy group which may have a substituent; and $R^1$ and $R^2$ are the same as those defined above];

(Step 5): a step for eliminating the substituent X present on the compound represented by the general formula (6) to thus form a compound represented by the following general formula (7):

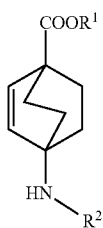

(7)

[in the formula (7), $R^1$ and $R^2$ are the same as those defined above]; and (Step 6): a step for reducing the compound represented by the general formula (7) to thus form a compound represented by the following general formula (8):

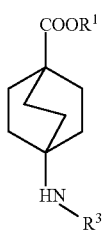

(8)

[in the formula (8), $R^3$ represents a hydrogen atom; an alkyl group having 1 to 6 carbon atoms, which may have a substituent; or an aralkyl group which may have a substituent; and $R^1$ is the same as that defined above].

[5] The process as set forth in the foregoing item [4], wherein $R^2$ represents a benzyl group, a p-methoxybenzyl group, a methoxy group, or a benzyloxy group; and $R^3$ represents a hydrogen atom.

[6] A process for production of a compound represented by the following general formula (8) comprising the following steps:

(Step 1): a step for reacting a compound represented by the following general formula (1):

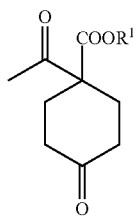

(1)

[in the formula (1), $R^1$ represents an alkyl group having 1 to 6 carbon atoms, which may have a substituent; an arylmethyl group which may have a substituent; or an arylethyl group which may have a substituent], with a compound represented by the following general formula (2):

$R^2$—$NH_2$ (2)

[in the formula (2), $R^2$ represents an alkyl group having 1 to 6 carbon atoms, which may have a substituent; an aralkyl group which may have a substituent; a hydroxyl group; an alkyloxy group having 1 to 6 carbon atoms, which may have a substituent; or an aralkyloxy group which may have a substituent], to thus form a compound represented by the following general formula (3):

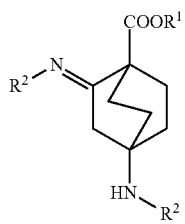

(3)

[in the formula (3), $R^1$ and $R^2$ are the same as those defined above];

(Step 2): a step for hydrolyzing the compound represented by the general formula (3) to form a compound represented by the following general formula (4):

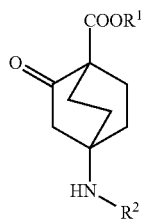

(4)

[in the formula (4), $R^1$ and $R^2$ are the same as those defined above];

(Step 3): a step for reducing the compound represented by the general formula (4) to thus form a compound represented by the following general formula (5):

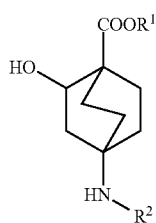

(5)

[in the formula (5), $R^1$ and $R^2$ are the same as those defined above];

(Step 4): a step for reacting the compound represented by the general formula (5) with a halogenating agent, an alkylsulfonating agent having 1 to 6 carbon atoms, which may have a substituent, or a benzenesulfonating agent which may have a substituent to thus form a compound represented by the following general formula (6):

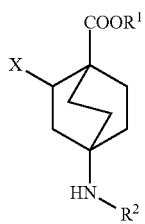

(6)

[in the formula (6), X represents a halogen atom, an alkylsulfonyloxy group having 1 to 6 carbon atoms, which may have a substituent, or a benzenesulfonyloxy group which may have a substituent; and R¹ and R² are the same as those defined above];

(Step 5): a step for eliminating the substituent X present on the compound represented by the general formula (6) to thus form a compound represented by the following general formula (7):

(7)

[in the formula (7), R¹ and R² are the same as those defined above]; and (Step 6): a step for reducing the compound represented by the general formula (7) to thus form a compound represented by the following general formula (8):

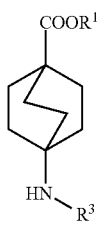

(8)

[in the formula (8), R³ represents a hydrogen atom; an alkyl group having 1 to 6 carbon atoms, which may have a substituent; or an aralkyl group which may have a substituent; and R¹ is the same as that defined above].

[7] The process as set forth in the foregoing item [6], wherein the amount of the compound represented by the general formula (2) is not less than 2 equivalents relative to that of the compound represented by the general formula (1).

[8] The process as set forth in the foregoing item [6] or [7], wherein R² represents a benzyl group, a p-methoxybenzyl group, a methoxy group, or a benzyloxy group; and R³ represents a hydrogen atom.

[9] A compound represented by the following general formula (3):

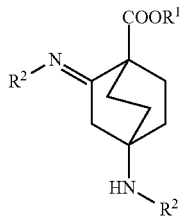

(3)

[in the formula (3), R¹ represents an alkyl group having 1 to 6 carbon atoms, which may have a substituent; an arylmethyl group which may have a substituent; or an arylethyl group which may have a substituent; and R² represents an alkyl group having 1 to 6 carbon atoms, which may have a substituent; an aralkyl group which may have a substituent; a hydroxyl group; an alkyloxy group having 1 to 6 carbon atoms, which may have a substituent; or an aralkyloxy group which may have a substituent].

[10] A compound represented by the following general formula (4):

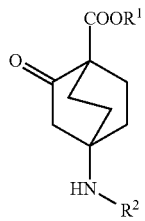

(4)

[in the formula (4), R¹ represents an alkyl group having 1 to 6 carbon atoms, which may have a substituent; an arylmethyl group which may have a substituent; or an arylethyl group which may have a substituent; and R² represents an alkyl group having 1 to 6 carbon atoms, which may have a substituent; an aralkyl group which may have a substituent; a hydroxyl group; an alkyloxy group having 1 to 6 carbon atoms, which may have a substituent; or an aralkyloxy group which may have a substituent].

[11] A compound represented by the following general formula (9):

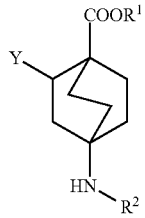

(9)

[in the formula (9), R¹ represents an alkyl group having 1 to 6 carbon atoms, which may have a substituent; an arylmethyl group which may have a substituent; or an arylethyl group which may have a substituent; R² represents an alkyl group having 1 to 6 carbon atoms, which may have a substituent; an aralkyl group which may have a substituent; a hydroxyl group; an alkyloxy group having 1 to 6 carbon atoms, which may have a substituent; or an aralkyloxy group which may have a substituent; and Y represents a hydroxyl group, a halogen atom, an alkylsulfonyloxy group having 1 to 6 carbon atoms, which may have a substituent, or a benzenesulfonyloxy group which may have a substituent].

[12] A compound represented by the following general formula (7):

(7)

[in the formula (7), R¹ represents an alkyl group having 1 to 6 carbon atoms, which may have a substituent; an arylmethyl group which may have a substituent; or an arylethyl group which may have a substituent; and $R^2$ represents an alkyl group having 1 to 6 carbon atoms, which may have a substituent; an aralkyl group which may have a substituent; a hydroxyl group; an alkyloxy group having 1 to 6 carbon atoms, which may have a substituent; or an aralkyloxy group which may have a substituent].

Effects of the Invention

According to the present invention, the compound represented by the general formula (8) can efficiently be prepared under mild conditions. As a result, the compound represented by the general formula (8) can be prepared in a large quantity at a low price.

MODE FOR CARRYING OUT THE INVENTION

The present invention will hereunder be described in more detail.

The phrase "an alkyl group having 1 to 6 carbon atoms" included in the passage "an alkyl group having 1 to 6 carbon atoms, which may have a substituent" used in this specification means a linear or branched alkyl group having 1 to 6 carbon atoms and specific examples thereof include a methyl group, an ethyl group, a propyl group, an isopropyl group, a butyl group, a hexyl group and the like.

The term "an arylmethyl group" included in the passage "an arylmethyl group which may have a substituent" used in this specification means a methyl group which is substituted with an aryl group, wherein the term "aryl group" means, for instance, a phenyl group, a naphthyl group an anthranyl group, and the like. Accordingly, specific examples of such "arylmethyl group" include a benzyl group, a naphthylmethyl group, and the like. In addition, the term "an arylethyl group" included in the passage "an arylethyl group which may have a substituent" used in this specification means an ethyl group which is substituted with an aryl group and specific examples thereof include a phenethyl group, a 1-phenylethyl group, and the like.

The term "an aralkyl group" included in the passage "an aralkyl group which may have a substituent" and used in this specification means an alkyl group having 1 to 6 carbon atoms which is substituted with an aryl group and specific examples thereof include a benzyl group, a phenethyl group, a 3-phenylpropyl group, and the like.

The phrase "an alkyloxy group having 1 to 6 carbon atoms, which may have a substituent" used in this specification means a group in which an alkyl group having 1 to 6 carbon atoms is bound to an oxygen atom and specific examples thereof include a methoxy group, an ethoxy group, a propyloxy group, an isopropyloxy group, and the like.

The term "an aralkyloxy group" included in the passage "an aralkyloxy group which may have a substituent" and used in this specification means a group in which an aralkyl group is bound to an oxygen atom and specific examples thereof are a benzyloxy group, a phenethyloxy group, and the like.

Alkylsulfonic acids having 1 to 6 carbon atoms which may have a substituent; acid anhydrides having 1 to 6 carbon atoms which may have a substituent, or acid halides having 1 to 6 carbon atoms which may have a substituent can be used as the foregoing "an alkylsulfonating agent having 1 to 6 carbon atoms, which may have a substituent" used in this specification and specific examples thereof include methanesulfonyl chloride, trifluoromethanesulfonyl chloride, and the like.

Usable herein as the "benzenesulfonating agents which may have a substituent" used in this specification are, for instance, benzenesulfonic acids which may have a substituent, acid anhydrides which may have a substituent or acid halides which may have a substituent and specific examples thereof are benzenesulfonyl chloride and toluenesulfonyl chloride, and the like.

The phrase "an alkylsulfonyloxy group having 1 to 6 carbon atoms" included in the passage "an alkylsulfonyloxy group having 1 to 6 carbon atoms, which may have a substituent" and used in this specification means a sulfonyloxy group which is substituted with an alkyl group having 1 to 6 carbon atoms. Accordingly, specific examples of the "an alkylsulfonyloxy group having 1 to 6 carbon atoms, which may have a substituent" include a methanesulfonyloxy group and a trifluoromethanesulfonyloxy group. The "substituent" of the foregoing "an alkyl group having 1 to 6 carbon atoms, which may have a substituent"; "an arylmethyl group which may have a substituent"; "an arylethyl group which may have a substituent"; "an aralkyl group which may have a substituent"; "an alkyloxy group having 1 to 6 carbon atoms, which may have a substituent"; and "an aralkyloxy group which may have a substituent" may be, for instance, a halogen atom, a hydroxyl group, an alkyl group having 1 to 6 carbon atoms; alkoxy groups having 1 to 6 carbon atoms; alkylcarbonyl groups having 1 to 6 carbon atoms; alkoxycarbonyl groups having 1 to 6 carbon atoms; alkylthio groups having 1 to 6 carbon atoms; alkylsulfinyl groups having 1 to 6 carbon atoms; alkylsulfonyl groups having 1 to 6 carbon atoms; amino groups; alkylamino groups having 1 to 6 carbon atoms; di-(alkyl having 1 to 6 carbon atoms)amino groups; 4- to 9-membered cyclic amino groups which may have 1 to 3 hetero atoms; formylamino groups; alkylcarbonylamino groups having 1 to 6 carbon atoms; alkoxycarbonylamino groups having 1 to 6 carbon atoms; alkylsulfonylamino groups having 1 to 6 carbon atoms; arylsulfonylamino groups which may have substituents; aralkyl groups which may have substituents; cyano group, and the like. Among them, preferably used herein include, for instance, halogen atoms, alkyl groups having 1 to 6 carbon atoms, alkoxy groups having 1 to 6 carbon atoms, alkoxycarbonyl groups having 1 to 6 carbon atoms, mono- or di-substituted alkylamino groups having 1 to 6 carbon atoms, 4- to 9-membered cyclic amino groups which may have 1 to 3 hetero atoms, alkylcarbonylamino groups having 1 to 6 carbon atoms; alkoxycarbonylamino groups having 1 to 6 carbon atoms; aralkyl groups which may have a substituent, and cyano group.

Moreover, as the substituents of the foregoing "an alkylsulfonating agent having 1 to 6 carbon atoms, which may be substituted with a substituent"; "a benzenesulfonating agent which may have a substituent"; "an alkylsulfonyloxy group having 1 to 6 carbon atoms, which may be substituted with a substituent"; and "a benzenesulfonyloxy group which may have a substituent," there can be listed, for instance, those specified below: Halogen atoms, alkyl groups having 1 to 6 carbon atoms, alkoxy groups having 1 to 6 carbon atoms, alkylcarbonyl groups having 1 to 6 carbon atoms, alkoxycarbonyl groups having 1 to 6 carbon atoms, alkylthio groups having 1 to 6 carbon atoms, alkylsulfinyl groups having 1 to 6 carbon atoms, alkylsulfonyl groups having 1 to 6 carbon atoms, alkylsulfonylamino groups having 1 to 6 carbon atoms, arylsulfonylamino groups which may have substituents, aralkyl groups which may have substituents, a nitro group, a cyano group, and the like, and among them, preferably used herein include, for instance, halogen atoms, alkyl groups having 1 to 6 carbon atoms, alkoxy groups having 1 to 6 carbon atoms, alkylcarbonyl groups having 1 to 6 carbon atoms, alkoxycarbonyl groups having 1 to 6 carbon atoms, alkylsulfonyl groups having 1 to 6 carbon atoms, alkylsulfonylamino groups having 1 to 6 carbon atoms, arylsulfonylamino groups which may have a substituent, aralkyl groups which may have a substituent, a nitro group and a cyano group.

The term "halogen atom" used herein means a fluorine, chlorine, bromine or iodine atom.

The term "halogenating agent" used herein means, for instance, thionyl chloride, phosphorus oxychloride, and the like.

The preparation process according to the present invention will be shown in scheme 1:

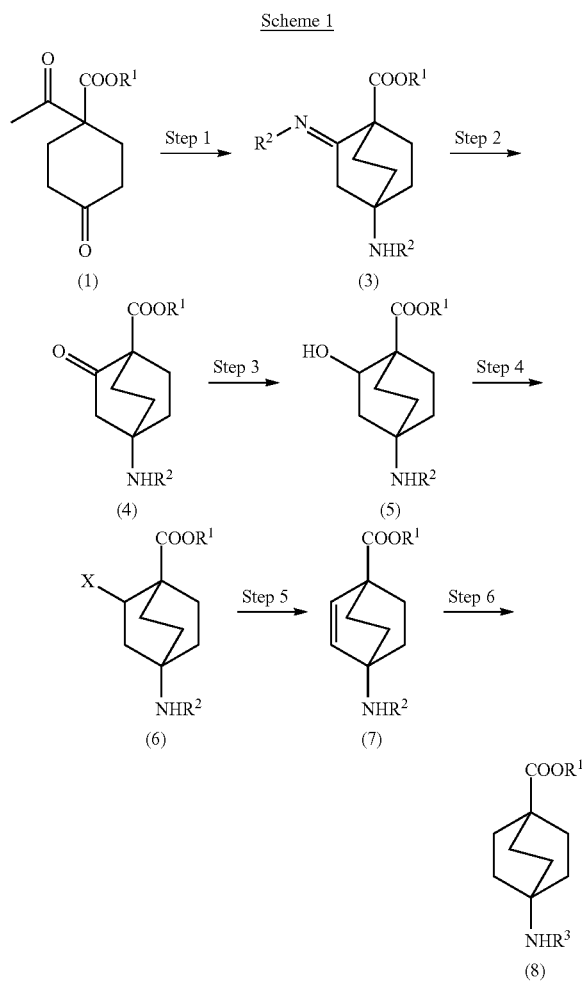

[in the formulas, $R^1$, $R^2$, $R^3$ and X are the same as defined above].

The compound represented by the general formula (1) per se as a raw material used in the present invention can be prepared according to the process disclosed in Non-Patent Document 1, 2, 3 or 5.

The step 1 is one in which a compound represented by the general formula (1) and a compound represented by the following general formula (2) are subjected to a ring-forming reaction to thus form a bicyclo[2.2.2]octane skeleton represented by the foregoing general formula (3):

$$R^2-NH_2 \quad (2)$$

[Wherein $R^2$ is the same as that specified above].

The reagents used in this reaction are as follows: Inorganic acids such as hydrochloric acid, hydrobromic acid, hydriodic acid, sulfuric acid, nitric acid, phosphoric acid and polyphosphoric acid; organic acids such as p-toluenesulfonic acid, methanesulfonic acid, trifluoroacetic acid, formic acid and acetic acid; and Lewis acids such as titanium tetrachloride, and preferably used herein include, for instance, toluenesulfonic acid, methanesulfonic acid or trifluoromethanesulfonic acid and more preferably used herein are, for instance, toluenesulfonic acid.

The reaction solvents to be used in this reaction are not restricted to any particular ones insofar as they are stable under the reaction conditions used in this reaction and they are inert so as not to prevent the progress of the reaction. Examples of such solvents include alcohols (such as methanol, ethanol, propanol, butanol and octanol), cellosolves (such as methoxyethanol and ethoxyethanol), aprotic polar organic solvents (such as dimethylformamide, dimethylsulfoxide, dimethylacetamide, tetramethyl urea, sulfolane, N-methylpyrrolidone and N,N-dimethylimidazolidinone), ethers (such as diethyl ether, diisopropyl ether, t-butyl methyl ether, tetrahydrofuran and dioxane), aliphatic hydrocarbons (such as pentane, hexane, cyclohexane, octane, decane, decalin and petroleum ether), aromatic hydrocarbons (such as benzene, chlorobenzene, o-dichlorobenzene, nitrobenzene, toluene, xylene, mesitylene and tetralin), halogenated hydrocarbons (such as chloroform, dichloromethane, dichloroethane and carbon tetrachloride), lower aliphatic acid esters (such as methyl acetate, ethyl acetate, butyl acetate and methyl propionate), alkoxyalkanes (such as dimethoxyethane and diethoxyethane), and nitriles (such as acetonitrile, propionitrile and butyronitrile). These solvents are appropriately selected while taking into consideration the easiness of the occurrence of the desired reaction and they may be used alone or in any combination. Optionally, they may be treated with an appropriate dehydrating agent or a drying agent in order to use them as anhydrous solvents. Preferably used in this step are those, which can form an azeotropic mixture and from which water can be separated, such as toluene and chlorobenzene among others, with toluene being more preferably used.

The amount of the acid to be used in this reaction ranges from 0.001 to 10 molar equivalents, preferably 0.001 to 1 molar equivalent and more preferably 0.005 to 0.02 molar equivalents, relative to that of the compound represented by the general formula (1). The reaction can be carried out at a temperature ranging from 25° C. to the reflux temperature of the solvent used and preferably the reflux temperature.

The foregoing step 2 is one in which the compound represented by the general formula (3) is hydrolyzed to give a compound represented by the general formula (4). This step 2 is preferably carried out under acidic conditions.

The acids capable of being used in this step 2 may be the same or different from those used in the foregoing step 1, specific examples thereof include inorganic acids such as hydrochloric acid, hydrobromic acid, hydriodic acid, sulfuric acid, nitric acid, phosphoric acid and polyphosphoric acid; and organic acids such as p-toluenesulfonic acid, methanesulfonic acid, trifluoroacetic acid, formic acid and acetic acid, with hydrochloric acid being preferably used in this step 2.

The reaction solvents to be used in this reaction step are not restricted to any particular ones insofar as they are stable under the reaction conditions used in this reaction and they are inert so as not to prevent the progress of the reaction. Examples of such solvents include water, alcohols (such as methanol, ethanol, propanol, butanol and octanol), cellosolves (such as methoxyethanol and ethoxy ethanol), aprotic polar organic solvents (such as dimethylformamide, dimethyl sulfoxide, dimethylacetamide, tetramethyl urea, sulfolane, N-methylpyrrolidone and N,N-dimethylimidazolidinone), ethers (such as diethyl ether, diisopropyl ether, t-butyl methyl ether, tetrahydrofuran and dioxane), aliphatic hydrocarbons (such as pentane, hexane, cyclohexane, octane, decane, decalin and petroleum ether), aromatic hydrocarbons (such as benzene, chlorobenzene, o-dichlorobenzene, nitrobenzene, toluene, xylene, mesitylene and tetralin), halogenated hydrocarbons (such as chloroform, dichloromethane, dichloroethane and carbon tetrachloride),
ketones (such as acetone, methyl ethyl ketone, methyl butyl ketone and methyl isobutyl ketone), lower aliphatic acid esters (such as methyl acetate, ethyl acetate, butyl acetate and methyl propionate), alkoxyalkanes (such as dimethoxyethane and diethoxyethane) and nitriles (such as acetonitrile, propionitrile and butyronitrile).

These solvents are appropriately selected while taking into consideration the easiness of the occurrence of the desired reaction and they may be used alone or in any combination. Moreover, they may optionally be treated with an appropriate dehydrating agent or a drying agent in order to use them as anhydrous solvents. Preferably used in this step include, for instance, a mixed solvent of toluene and water.

The amount of the acid to be used in this step ranges from 0.01 to 10 molar equivalents and preferably 1 to 5 molar equivalents relative to that of the compound represented by the general formula (1). The reaction can be carried out at a temperature ranging from 0° C. to the reflux temperature of the solvent used and preferably 5 to 65° C.

The step 1 and 2 may be carried out separately or continuously. More specifically, the step 2 may be carried out after the compound represented by the general formula (3) prepared in the step 1 is isolated or the step 2 may be carried out without isolating the compound represented by the general formula (3) prepared in the step 1.

In the step 1, it is preferred to use the compound represented by the general formula (2) in an amount of not less than 2 molar equivalents relative to the compound represented by the general formula (1).

Incidentally, Non-Patent Document 1 discloses that the same ring-forming reaction can proceed when using a secondary amine having a cyclic structure. In the ring-forming reaction disclosed therein, however, an amine derivative is used in an amount on the order of about 1.3 equivalents. In this respect, the inventors of this invention have found that the compound represented by the general formula (4) cannot be obtained in any satisfactory yield even when the reaction is carried out according to the process disclosed in the article while using an amine derivative represented by the general formula (2).

For this reason, in the step 1, the compound represented by the general formula (2) is preferably used in an amount of not less than 2 molar equivalents relative to the compound represented by the general formula (1), in order to produce the compound represented by the general formula (4) in a satisfactory yield.

The foregoing step 3 is one in which the compound represented by the general formula (4) thus prepared in the step 2 is reduced to form an alcohol derivative represented by the general formula (5).

Used as the reducing agents in this step include, for instance, sodium boron hydride and reducing agents similar thereto, lithium aluminum hydride and reducing agents similar thereto, diborane and those analogous to the same, alkylsilanes and reducing agents similar thereto, organo-tin compounds, dissolved alkali metals, hydrogenation catalysts used in hydrogen gas atmosphere, and microorganisms having a reducing ability (microbial reduction technique), and the step 3 is preferably carried out with the use of sodium boron hydride.

The reaction solvents to be used in this reaction step are not restricted to particular ones, in respect of the kind thereof, insofar as they are stable under the reaction conditions used in this step and they are inert so as not to prevent the progress of the reaction. Examples of such solvents include alcohols (such as methanol, ethanol, propanol, butanol and octanol), cellosolves (such as methoxyethanol and ethoxyethanol), aprotic polar organic solvents (such as dimethylformamide, dimethylsulfoxide, dimethylacetamide, tetramethyl urea, sulfolane, N-methylpyrrolidone and N,N-dimethylimidazolidinone), ethers (such as diethyl ether, diisopropyl ether, t-butyl methyl ether, tetrahydrofuran and dioxane), aliphatic hydrocarbons (such as pentane, hexane, cyclohexane, octane, decane, decalin and petroleum ether), aromatic hydrocarbons (such as benzene, chlorobenzene, o-dichlorobenzene, nitrobenzene, toluene, xylene, mesitylene and tetralin), halogenated hydrocarbons (such as chloroform, dichloromethane, dichloroethane and carbon tetrachloride), alkoxyalkanes (such as dimethoxyethane and diethoxyethane) and nitriles (such as acetonitrile, propionitrile and butyronitrile).

These solvents are appropriately selected while taking into consideration the easiness of the occurrence of the desired reaction and they may be used alone or in any combination. Moreover, they may optionally be treated with an appropriate dehydrating agent or a drying agent in order to use them as anhydrous solvents. Preferably used in this step include, for instance, ethanol and a mixed solvent of toluene and ethanol, among others.

The amount of the foregoing reducing agent to be used in this step ranges from 0.4 to 10 molar equivalents and preferably 0.4 to 2 molar equivalents relative to that of the compound represented by the general formula (4). The reaction can be carried out at a temperature ranging from −10° C. to the reflux temperature of the solvent used and preferably ice-cooled temperature to room temperature.

The step 4 is one in which the hydroxyl group of the compound represented by the general formula (5) is converted into a leaving group to thus form a compound represented by the general formula (6).

Such a leaving group usable in this step may be, for instance, a halogen atom, an alkylsulfonyloxy group having 1 to 6 carbon atoms, which may have a substituent, or a benzenesulfonyloxy group which may have a substituent. Preferably used herein as such leaving groups are, for instance, benzene sulfonyloxy group, toluenesulfonyloxy group, methanesulfonyloxy group, and trifluoromethanesulfonyl group, with methanesulfonyloxy group being more preferably used herein.

When using a halogen atom as such a leaving group, usable herein as such halogenating agents include thionyl chloride, phosphorus oxychloride, and the like. Examples of alkylsulfonating agents having 1 to 6 carbon atoms which may have a substituent include alkylsulfonic acids having 1 to 6 carbon atoms which may have a substituent, acid anhydrides having 1 to 6 carbon atoms which may have a substituent and acid halides having 1 to 6 carbon atoms which may have a substituent and specific examples thereof are methanesulfonyl chloride and trifluoromethanesulfonyl chloride, with methanesulfonyl chloride being preferably used herein.

Benzenesulfonating agents which may have a substituent may be, for instance, benzenesulfonic acid which may have a substituent, acid anhydrides which may have a substituent and acid halides which may have a substituent and specific examples thereof are benzenesulfonyl chloride, 4-methylbenzenesylfonyl chloride, and the like.

When using a methanesulfonyloxy group as the leaving group, the methanesulfonylating agent to be used may be, for instance, a methanesulfonyl halide, methanesulfonic acid or methanesulfonic anhydride and the methanesulfonylating agent is preferably methanesulfonyl chloride. The reaction is preferably carried out under basic conditions and the base to be used may be an organic base or an inorganic base. Specific examples of organic bases include amines such as diethylamine, triethylamine, diisopropylethylamine, tri-n-propyl amine, tri-n-butylamine, DBN (diazabicyclononane), DBU (diazabicycloundecene), N-methylmorpholine, and N,N-dimethylaniline; pyridines such as pyridine, methylethylpyridine, lutidine, 4-N,N-dimethylaminopyridine; imidazoles and pyrazoles. Specific examples of the inorganic bases usable herein include hydroxides of alkali metals or alkaline earth metals such as lithium hydroxide, sodium hydroxide, potassium hydroxide, magnesium hydroxide, calcium hydroxide and barium hydroxide; carbonates of alkali metals or alkaline earth metals such as sodium carbonate, potassium carbonate, cesium carbonate, magnesium carbonate, calcium carbonate and barium carbonate; metal alkoxides such as sodium ethoxide; alkali metal amides such as sodium amide and lithium amide; and alkali metal hydrides such as sodium hydride and lithium hydride. The bases to be used herein are preferably organic bases, with triethylamine being more preferably used.

The reaction solvents to be used in this reaction step are not restricted to any particular ones, in respect of the kind thereof, insofar as they are stable under the reaction conditions used in this step and they are inert so as not to prevent the progress of the reaction. Examples of such solvents include cellosolves (such as methoxyethanol and ethoxyethanol), ethers (such as diethyl ether, diisopropyl ether, t-butyl methyl ether, tetrahydrofuran and dioxane), aliphatic hydrocarbons (such as pentane, hexane, cyclohexane, octane, decane, decalin and petroleum ether), aromatic hydrocarbons (such as benzene, chlorobenzene, o-dichlorobenzene, nitrobenzene, toluene, xylene, mesitylene and tetralin), halogenated hydrocarbons (such as chloroform, dichloromethane, dichloroethane and carbon tetrachloride), ketones (such as acetone, methyl ethyl ketone, methyl butyl ketone and methyl isobutyl ketone), lower aliphatic acid esters (such as methyl acetate,
ethyl acetate, butyl acetate and methyl propionate), alkoxyalkanes (such as dimethoxyethane and diethoxyethane) and nitriles (such as acetonitrile, propionitrile and butyronitrile). These solvents are appropriately selected while taking into consideration the easiness of the occurrence of the desired reaction and they may be used alone or in any combination. Moreover, they may optionally be treated with an appropriate dehydrating agent or a drying agent in order to use them as anhydrous solvents. The reaction of this step 4 is preferably carried out in a mixed solvent comprising toluene and tetrahydrofuran, among others.

The amount of the foregoing methanesulfonylating agents to be used in this step ranges from 1 to 2.0 molar equivalents and preferably 1 to 2 molar equivalents relative to that of the compound represented by the general formula (5). On the other hand, the amount of the base to be used ranges from 0.1 to 10 molar equivalents and preferably 1 to 1.5 molar equivalents relative to that of the compound represented by the general formula (5). The reaction can be carried out, in this reaction step, at a temperature ranging from −80° C. to the reflux temperature of the solvent used and preferably 0 to 100° C. and more preferably room temperature.

The foregoing step 5 is one in which the compound represented by the general formula (6) is converted into a compound represented by the general formula (7).

This reaction is preferably carried out under basic conditions. The base to be used in the reaction may be an organic base or an inorganic base. Specific examples of organic bases include amines such as diethylamine, triethylamine, diisopropylethylamine, tri-n-propylamine, tri-n-butylamine, DBN (diazabicyclo nonane), DBU (diazabicycloundecene), N-methylmorpholine and N,N-dimethyl aniline; pyridines such as pyridine, methylethylpyridine, lutidine, 4-N,N-dimethyl aminopyridine; imidazoles and pyrazoles; and inorganic bases, for instance, hydroxides of alkali metals or alkaline earth metals such as lithium hydroxide, sodium hydroxide, potassium hydroxide, magnesium hydroxide, calcium hydroxide and barium hydroxide; carbonates of alkali metals or alkaline earth metals such as sodium carbonate, potassium carbonate, cesium carbonate, magnesium carbonate, calcium carbonate and barium carbonate; metal alkoxides such as sodium methoxide and potassium t-butoxide; alkali metal amides such as sodium amide and lithium amide; and alkali metal hydrides such as sodium hydride and lithium hydride. The base preferably used in the reaction is DBU (diazabicycloundecene).

The reaction solvents to be used in this reaction step are not restricted to any particular ones, in respect of the kind thereof, insofar as they are stable under the reaction conditions used in this step and they are inert so as not to prevent the progress of the reaction. Examples of such solvents include water, alcohols (such as methanol, ethanol, propanol, butanol and octanol), cellosolves (such as methoxyethanol and ethoxyethanol), aprotic polar organic solvents (such as dimethylformamide, dimethylsulfoxide, dimethylacetamide, tetramethyl urea, sulfolane, N-methylpyrrolidone and N,N-dimethylimidazolidinone), ethers (such as diethyl ether, diisopropyl ether, t-butyl methyl ether, tetrahydrofuran and dioxane), aliphatic hydrocarbons (such as pentane, hexane, cyclohexane, octane, decane, decalin and petroleum ether), aromatic hydrocarbons (such as benzene, chlorobenzene, o-dichlorobenzene, nitrobenzene, toluene, xylene, mesitylene and tetralin), halogenated hydrocarbons (such as chloroform, dichloromethane, dichloroethane and carbon tetrachloride), ketones (such as acetone, methyl ethyl ketone, methyl butyl ketone and methyl isobutyl ketone), lower aliphatic acid esters (such as methyl acetate, ethyl acetate, butyl acetate and methyl propionate), alkoxyalkanes (such as dimethoxyethane and diethoxyethane) and
nitriles (such as acetonitrile, propionitrile and butyronitrile). These solvents are appropriately selected while taking into consideration the easiness of the occurrence of the desired reaction and they may be used alone or in any combination. Moreover, they may optionally be treated with an appropriate dehydrating agent or a drying agent in order to use them as anhydrous solvents. Preferably used in this reaction include, for instance, toluene and dimethylacetamide, among others. It is not always necessary, in this reaction, to add additives, but the reaction is preferably carried out in the presence of an additive and such an additive usable herein includes, for instance, a halide of an alkali metal or an alkaline earth metal. In this respect, preferably used herein is an iodide of an alkali metal or alkaline earth metal. The amount of the foregoing base to be used ranges from 1 to 10 molar equivalents and preferably 1 to 6 molar equivalents relative to that of the compound represented by the general formula (6). On the other hand, the amount of the foregoing additive to be used ranges from 0.01 to 10 molar equivalents and preferably 0.1 to 5 molar equivalents relative to that of the compound represented by the general formula (6). The reaction can be carried out, in this step, at a temperature ranging from 25° C. to the reflux temperature of the solvent used and preferably the reflux temperature.

The step 6 corresponds to one in which the compound represented by the general formula (7) is reduced to form a compound represented by the general formula (8).

This step can be carried out according to the catalytic reduction under hydrogen gas atmosphere; the reduction with an alkali metal or an alkaline earth metal; the reduction with a metal hydride; the reduction with a diimide; or the electrolytic reduction, and it can preferably be carried out according to the catalytic reduction under hydrogen gas atmosphere.

The compound of formula (7) can be reduced, according to the catalytic reduction technique, while making use of a homogeneous catalyst such as chlorotris(triphenylphosphine) rhodium(I) or a heterogeneous catalyst such as palladium/carbon or platinum/carbon and the reduction can preferably be carried out using palladium/carbon as a catalyst. The reaction solvents to be used in this reduction step are not restricted to particular ones, in respect of the kind thereof, insofar as they are stable under the reaction conditions used in this step and they are inert so as not to prevent the progress of the reaction. Examples of such solvents include water, alcohols (such as methanol, ethanol, propanol, butanol and octanol), cellosolves (such as methoxyethanol and ethoxyethanol), aprotic polar organic solvents (such as dimethylformamide, dimethylacetamide, tetramethyl urea, N-methylpyrrolidone and N,N-dimethylimidazolidinone), ethers (such as diethyl ether, diisopropyl ether, t-butyl methyl ether, tetrahydrofuran and dioxane), aliphatic hydrocarbons (such as pentane, hexane, cyclohexane, octane, decane, decalin and petroleum ether), aromatic hydrocarbons (such as benzene, chlorobenzene, o-dichlorobenzene, nitrobenzene, toluene, xylene, mesitylene and tetralin),
halogenated hydrocarbons (such as chloroform, dichloromethane, dichloroethane and carbon tetrachloride), ketones (such as acetone, methyl ethyl ketone, methyl butyl ketone and methyl isobutyl ketone), lower aliphatic acid esters (such as methyl acetate, ethyl acetate, butyl acetate and methyl propionate), alkoxyalkanes (such as dimethoxyethane and diethoxyethane) and nitriles (such as acetonitrile, propionitrile and butyronitrile). These solvents are appropriately selected while taking into consideration the easiness of the occurrence of the desired reaction and they may be used alone or in any combination. Moreover, they may optionally be treated with an appropriate dehydrating agent or a drying agent and they can thus be used as anhydrous solvents. Preferably used in this reaction includes, for instance, ethanol, among others. The amount of the catalyst to be used ranges from 0.001 to 10 times and preferably 0.001 to 0.3 times that of the compound represented by the general formula (7). The reaction can be carried out, in this step, at a temperature ranging from −10° C. to the reflux temperature of the solvent used and the reaction is preferably carried out at room temperature.

If the substituent $R^2$ in the general formula (7) represents a benzyl group, a p-methoxybenzyl group, a methoxy group or a benzyloxy group, the reduction of the compound of formula (7) permits the direct formation of a compound represented by the general formula (8) in which $R^3$ represents a hydrogen atom. Accordingly, to obtain a compound of formula (8) in which $R^3$ is a hydrogen atom, the substituent $R^2$ in formula (7) is preferably a benzyl group, a p-methoxybenzyl group, a methoxy group or a benzyloxy group and the substituent $R^2$ is further preferably a benzyl group.

The process disclosed in Non-Patent Document 1 requires the use of a low temperature reaction and accordingly, it is not suitable for the large-scale synthesis of any target product. In addition, if it is intended to prepare a compound represented by the general formula (8) starting from a compound represented by the general formula (4), according to the processes disclosed in Non-Patent Documents 2 to 6, the reaction would be accompanied by the production of a large number of decomposition products and accordingly, these processes would be considered as impractical. According to the present invention, however, each step would proceed in a high yield, permit the large-scale production of a target compound and therefore, the process of the present invention permits the efficient production of a compound represented by the general formula (8), while using simple production facilities.

The reagents, acids, bases, solvents or the like specifically disclosed above are simply illustrative ones to be used in the practice of the present invention and accordingly, the present invention is not restricted to these specific conditions at all.

EXAMPLES

The production process according to the present invention will hereunder be described with reference to the following Examples, but the scope of the present invention is, by no means, limited to these Examples.

In this connection, $^1$H-NMR spectra were determined at 300 MHz and LC, LC/MS, GC and GC/MS were determined under the following conditions, respectively.

In this respect, the abbreviations NMR, LC, LC/MS, GC and GC/MS represent the nuclear magnetic resonance spectroscopic technique; the liquid chromatography technique; the liquid chromatography/mass spectroscopic analysis technique; the gas chromatography technique; and the gas chromatography/mass spectroscopic analysis technique, respectively.

Example of the Conditions for LC:
Column Used: XBridge C18 (3.5 μm, 4.6×150 mm) available from Waters Company;
Eluting Solution: 20 mM Ammonium hydrogen carbonate aqueous solution/acetonitrile (50/50).
Example of the Conditions for LC/MS:
Column Used: XBridge (5 μm, 2.1×150 mm) available from Waters Company;
Eluting Solution: Acetonitrile/0.1% ammonium hydrogen carbonate aqueous solution (40/60).
Example of the Conditions for GC:
Column Used: DB-5 (0.25 μm, 0.25 mm×30 m) available from Agilent Company;
Column Temperature: 100° C. (one minute)→10° C./min→250° C. (10 minutes).
Example of the Conditions for GC/MS:
Column Used: DB-5MS (0.25 μm, 0.25×30 m) available from Agilent Company;
Column Temperature: 50° C. (5 minutes)→10° C./min→250° C. (30 minutes).
Example of Quantitative Analysis (Quantitative Analysis Technique)

A desired product to be analyzed (a specimen containing about 20 mg of the same) was correctly dispensed into a 50 mL volume measuring flask, there was further added a solution of internal standard substance (5 mL) to the specimen and then the total volume thereof was adjusted with the use of acetonitrile. The resulting sample was used in the LC or GC analysis.

Example 1

(Steps 1 and 2): 4-(Benzylamino)-2-oxobicyclo[2.2.2]octane-1-carboxylic acid ethyl ester Toluene (100 mL) was added to 1-acetyl-4-oxocyclohexyl carboxylic acid ethyl ester (8.0 g, 38 mmol) and then the resulting mixture was stirred. To the mixture, there were added benzylamine (5.3 mL, 49 mmol) and p-toluenesulfonic acid monohydrate (76 mg, 0.40 mmol). The mixture was refluxed for 8 hours with a Dean-Stark apparatus under the dehydration conditions. After cooled to room temperature, the mixture was concentrated under reduced pressure to give a crude product. The resulting crude product was treated according to the silica gel column chromatography (eluting solution: hexane/ethyl acetate) to thus obtain a mixture of the desired product and an imine derivative thereof. The mixture was dissolved in chloroform (200 mL) and then the resulting solution was treated with a 0.5 mol/L hydrochloric acid solution (100 mL). The suspended organic phase was separated, then treated with a 5% aqueous solution of sodium hydrogen carbonate and then separated. The organic phase was dried over anhydrous magnesium sulfate, followed by the removal of the drying agent through filtration and the subsequent concentration of the resulting filtrate under reduced pressure to thus give the desired product as a white solid. (2.9 g; yield: 26%).

$^1$H-NMR (300 MHz, ppm in $CDCL_3$) δ: 1.27 (t, 3H), 1.75-1.89 (m, 4H), 1.95-2.10 (m, 2H), 2.20-2.30 (m, 2H), 2.45 (s, 2H), 3.74 (s, 2H), 4.21 (q, 2H), 7.21-7.40 (m, 5H).
LC/MS (ESI+) m/z: 302 (MH+).
GC/MS (CI) m/z: 302 (MH+).
Analysis of Imine Derivative:
LC/MS (ESI+) m/z: 391 (MH+).
GC/MS (CI) m/z: 391 (MH+).

Example 2

(Steps 1 and 2): 4-(Benzylamino)-2-oxobicyclo[2.2.2]octane-1-carboxylic acid ethyl ester Toluene (130 mL) was added to 1-acetyl-4-oxocyclohexyl carboxylic acid ethyl ester (12.9 g, 60.6 mmol) and then the resulting mixture was stirred. To the mixture, there were added benzylamine (13.3 mL, 121 mmol) and p-toluenesulfonic acid monohydrate (124 mg, 0.65 mmol). The mixture was refluxed for 7 hours with a Dean-Stark apparatus under the dehydration conditions. After cooled back to room temperature, a 1 mol/L hydrochloric acid solution (130 mL) was added to the flask and the resulting mixture was then stirred for 0.5 hours. The mixture was made alkali by the use of a 2 mol/L sodium hydroxide aqueous solution, followed by the separation of the organic phase and the subsequent quantitative analysis (according to the LC technique). As a result, the yield of the desired product was found to be 75% (the internal standard substance used was 1,2,4-trimethyl benzene).

Example 3

(Steps 1 and 2): 4-(Benzylamino)-2-oxobicyclo[2.2.2]octane-1-carboxylic acid ethyl ester Toluene (310 mL) was added to 1-acetyl-4-oxocyclohexyl carboxylic acid ethyl ester (31.0 g, 146 mmol) and then the resulting mixture was stirred. To the mixture, there were added benzylamine (48.0 mL, 438 mmol) and p-toluenesulfonic acid monohydrate (251 mg, 1.32 mmol). The mixture was refluxed for 7 hours with a Dean-Stark apparatus under the dehydration conditions. The mixture was cooled to 20° C., a 3 mol/L hydrochloric acid solution (155 g) was added dropwise to the mixture and then the resulting mixture was stirred for 0.5 hours. To the mixture, there was added dropwise a 6 mol/L aqueous sodium hydroxide solution, followed by stirred for 10 minutes and the organic phase was separated. The resulting organic phase was washed twice with 155 g of a 18% aqueous ammonium chloride solution and further washed with 62 g of water. The organic phase was subjected to quantitative analysis (according to the LC technique) and as a result, the yield of the desired product was found to be 95% (the internal standard substance used was m-xylene).

Example 4

(Step 3): 4-(Benzylamino)-2-hydroxybicyclo[2.2.2]octane-1-carboxylic acid ethyl ester Ethanol (2 mL) was added to 4-(benzylamino)-2-oxobicyclo-[2.2.2]octane-1-carboxylic acid ethyl ester (200 mg, 0.66 mmol) and then the resulting mixture was stirred. The resulting mixture was cooled to 0° C., sodium boron hydride (38 mg, 1 mmol) was added thereto, the temperature thereof was raised up to room temperature and then the mixture was stirred for 30 minutes. After quenching the reaction mixture with a 18% aqueous ammonium chloride solution, the mixture was made uniform with water and acetonitrile and then quantitatively analyzed (according to the LC technique). As a result, the yield of the desired product was found to be 83% (the internal standard substance used was 1,2,4-trimethylbenzene).

$^1$H-NMR (300 MHz, ppm in $CDCL_3$) δ: 1.26 (t, 3H), 1.40-2.30 (m, 10H), 3.13 (brs, 1H), 3.70 (s, 2H), 4.15 (q, 2H), 4.35 (dd, 1H), 7.33-7.40 (m, 5H).
LC/MS (ESI+) m/z: 304 (MH+).
GC/MS (CI) m/z: 304 (MH+).

Example 5

(Step 4): 4-(Benzylamino)-2-(methylsulfonyloxy)bicyclo[2.2.2]octane-1-carboxylic acid ethyl ester To 4-(benzylamino)-2-hydroxybicyclo[2.2.2]octane-1-carboxylic acid ethyl ester (6.0 g, 19.8 mmol), there were added toluene (42.0 g), tetrahydrofuran (10.8 g) and triethylamine (4.0 g, 39.6 mmol) and then the resulting mixture was stirred. Methanesulfonyl chloride (2.9 g, 24.9 mmol) was added dropwise to the mixture, followed by the stirring thereof for one hour and 30 minutes. After quenching the reaction mixture with water, the resulting mixture was subjected to extraction procedures and the organic phase was quantitatively analyzed (according to the LC technique). As a result, the yield of the desired product was found to be 100% (the internal standard substance used was m-xylene).

$^1$H-NMR (300 MHz, ppm in $CDCL_3$) δ: 1.20 (t, 3H), 1.40-2.30 (m, 8H), 2.94 (s, 3H), 3.62 (s, 2H), 4.08 (q, 2H), 5.15 (dd, 1H), 7.33-7.35 (m, 5H).
LC/MS (ESI+) m/z: 382 (MH+).

Example 6

(Step 5): 4-(Benzylamino)bicyclo[2.2.2]-2-octene-1-carboxylic acid ethyl ester

To 2.27 g of a solution of 4-(benzylamino)-2-(methylsulfonyloxy)bicyclo[2.2.2]octane-1-carboxylic acid ethyl ester (1.0 g, 2.6 mmol) in toluene, there were added sodium iodide (78.6 mg, 0.52 mmol), toluene (9.3 g) and N,N-dimethyl acetamide (3.7 g) and the resulting mixture was stirred. Diazabicycloundecene (2.0 g, 13.1 mmol) was added to the mixture, followed by stirred for 43 hours at 120° C. After the reaction mixture was quenched with a 18% aqueous ammonium chloride solution, the resulting mixture was subjected to extraction procedures and the organic phase was quantitatively analyzed (according to the LC technique). As a result, the yield of the desired product was found to be 88% (the internal standard substance used was biphenyl).

$^1$H-NMR (300 MHz, ppm in $CDCL_3$) δ: 1.29 (t, 3H), 1.50-1.80 (m, 6H), 1.96 (m, 2H), 3.87 (s, 2H), 4.20 (q, 2H), 6.34 (d, 1H), 6.45 (d, 1H), 7.33-7.45 (m, 5H).

LC/MS (ESI+) m/z: 286 (MH+).

Example 7

(Step 6): 4-Aminobicyclo[2.2.2]octane-1-carboxylic acid ethyl ester

To 0.7 g of a solution of 4-(benzylamino)bicyclo[2.2.2]-2-octene-1-carboxylic acid ethyl ester (0.30 g, 1.1 mmol) in toluene, there was added ethanol (3.0 g) and the replacement was made with a nitrogen gas. To the mixture, there was added palladium/carbon (60 mg) and the replacement was made with a nitrogen gas and then a hydrogen gas. After the reaction mixture was stirred at room temperature for 7 hours, it was filtered and the filtrate was subjected to quantitative analysis. As a result, the yield of the desired product was found to be 96% (according to the absolute quantitative analysis process).

LC/MS (ESI+) m/z: 198 (MH+).
GC/MS (CI) m/z: 198 (MH+).

INDUSTRIAL APPLICABILITY

According to the present invention, there can be provided a process for production of a bicyclo[2.2.2]octylamine derivative, which is quite efficient and can produce the derivative in a large-scale while using mild reaction conditions and therefore, the present invention would industrially be applicable.

What is claimed is:

1. A process for production of a compound represented by the following general formula (4) comprising the following steps:

(Step1) a step for reacting a compound represented by the following general formula (1):

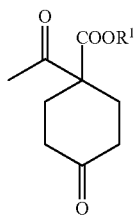

(1)

[in the formula (1), $R^1$ represents an alkyl group having 1 to 6 carbon atoms, which may have a substituent; an arylmethyl group which may have a substituent; or an arylethyl group which may have a substituent], with a compound represented by the following general formula (2):

$R^2-NH_2$ (2)

[in the formula (2), $R^2$ represents an alkyl group having 1 to 6 carbon atoms, which may have a substituent; an aralkyl group which may have a substituent; a hydroxyl group; an alkyloxy group having 1 to 6 carbon atoms, which may have a substituent; or an aralkyloxy group which may have a substituent], to thus form a compound represented by the following general formula (3):

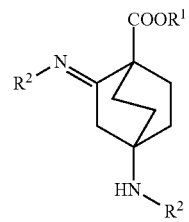

(3)

[in the formula (3), $R^1$ and $R^2$ are the same as those defined above]; and (Step 2) a step for hydrolyzing the compound represented by the general formula (3) to form a compound represented by the following general formula (4):

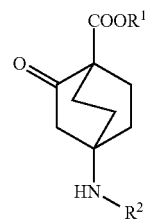

(4)

[in the formula (4), $R^1$ and $R^2$ are the same as those defined above].

2. The process as set forth in claim 1, wherein the amount of the compound represented by the general formula (2) is not less than 2 equivalents relative to that of the compound represented by the general formula (1).

3. The process as set forth in claim 1, wherein the compound represented by the general formula (3) is hydrolyzed in the presence of an acid.

4. A process for production of a compound represented by the following general formula (8) comprising the following steps:

(Step 3) a step for reducing a compound represented by the following general formula (4):

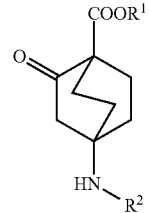

(4)

[in the formula (4), $R^1$ represents an alkyl group having 1 to 6 carbon atoms, which may have a substituent; an arylmethyl group which may have a substituent; or an arylethyl group which may have a substituent; and $R^2$ represents an alkyl group having 1 to 6 carbon atoms, which may have a substituent; an aralkyl group which may have a substituent; a hydroxyl group; an alkyloxy group having 1 to 6 carbon atoms, which may have a substituent; or an aralkyloxy group which may have a substituent], to thus form a compound represented by the following general formula (5):

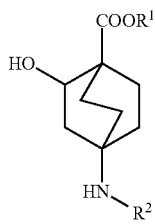

(5)

[in the formula (5), $R^1$ and $R^2$ are the same as those defined above];

(Step 4) a step for reacting the compound represented by the general formula (5) with a halogenating agent, an alkylsulfonating agent having 1 to 6 carbon atoms, which may have a substituent, or a benzenesulfonating agent which may have a substituent, to thus form a compound represented by the following general formula (6):

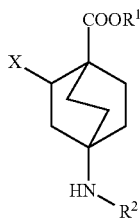

(6)

[in the formula (6), X represents a halogen atom, an alkylsulfonyloxy group having 1 to 6 carbon atoms, which may have a substituent, or a benzenesulfonyloxy group which may have a substituent; and
$R^1$ and $R^2$ are the same as those defined above];

(Step 5) a step for eliminating the substituent X present on the compound represented by the general formula (6) to thus form a compound represented by the following general formula (7):

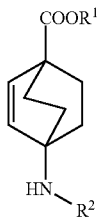

(7)

[in the formula (7), $R^1$ and $R^2$ are the same as those defined above]; and (Step 6) a step for reducing the compound represented by the general formula (7) to thus form a compound represented by the following general formula (8):

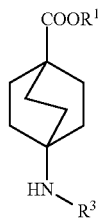

(8)

[in the formula (8), $R^3$ represents a hydrogen atom; an alkyl group having 1 to 6 carbon atoms, which may have a substituent; or an aralkyl group which may have a substituent; and
$R^1$ is the same as that defined above].

5. The process as set forth in claim 4, wherein $R^2$ represents a benzyl group, a p-methoxybenzyl group, a methoxy group, or a benzyloxy group; and
$R^3$ represents a hydrogen atom.

6. A process for production of a compound represented by the following general formula (8) comprising the following steps:

(Step 1) a step for reacting a compound represented by the following general formula (1):

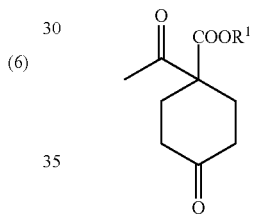

(1)

[in the formula (1), $R^1$ represents an alkyl group having 1 to 6 carbon atoms, which may have a substituent; an arylmethyl group which may have a substituent; or an arylethyl group which may have a substituent], with a compound represented by the following general formula (2):

(2)

[in the formula (2), $R^2$ represents an alkyl group having 1 to 6 carbon atoms, which may have a substituent; an aralkyl group which may have a substituent; a hydroxyl group; an alkyloxy group having 1 to 6 carbon atoms, which may have a substituent; or an aralkyloxy group which may have a substituent], to thus form a compound represented by the following general formula (3):

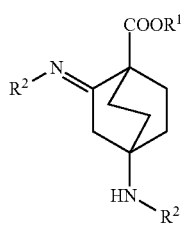

(3)

[in the formula (3), $R^1$ and $R^2$ are the same as those defined above];

(Step 2) a step for hydrolyzing the compound represented by the general formula (3) to form a compound represented by the following general formula (4):

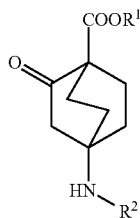

(4)

[in the formula (4), $R^1$ and $R^2$ are the same as those defined above];

(Step 3) a step for reducing the compound represented by the general formula (4) to thus form a compound represented by the following general formula (5):

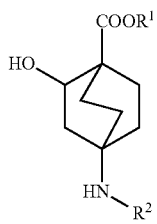

(5)

[in the formula (5), $R^1$ and $R^2$ are the same as those defined above];

(Step 4) a step for reacting the compound represented by the general formula (5) with a halogenating agent, an alkylsulfonating agent having 1 to 6 carbon atoms, which may have a substituent, or a benzenesulfonating agent which may have a substituent to thus form a compound represented by the following general formula (6):

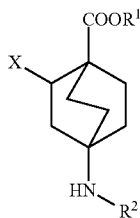

(6)

[in the formula (6), X represents a halogen atom, an alkylsulfonyloxy group having 1 to 6 carbon atoms, which may have a substituent, or a benzenesulfonyloxy group which may have a substituent; and
$R^1$ and $R^2$ are the same as those defined above];

(Step 5) a step for eliminating the substituent X present on the compound represented by the general formula (6) to thus form a compound represented by the following general formula (7):

(7)

[in the formula (7), $R^1$ and $R^2$ are the same as those defined above]; and (Step 6) a step for reducing the compound represented by the general formula (7) to thus form a compound represented by the following general formula (8):

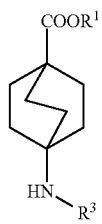

(8)

[in the formula (8), $R^3$ represents a hydrogen atom; an alkyl group having 1 to 6 carbon atoms, which may have a substituent; or an aralkyl group which may have a substituent; and
$R^1$ is the same as that defined above].

7. The process as set forth in claim 6, wherein the amount of the compound represented by the general formula (2) is not less than 2 equivalents relative to that of the compound represented by the general formula (1).

8. The process as set forth in claim 6, wherein $R^2$ represents a benzyl group, a p-methoxybenzyl group, a methoxy group, or a benzyloxy group; and $R^3$ represents a hydrogen atom.

9. The process as set forth in claim 2, wherein the compound represented by the general formula (3) is hydrolyzed in the presence of an acid.

10. The process as set forth in claim 7, wherein $R^2$ represents a benzyl group, a p-methoxybenzyl group, a methoxy group, or a benzyloxy group; and
$R^3$ represents a hydrogen atom.

\* \* \* \* \*